US 6,340,348 B1
Jan. 22, 2002

(54) CONTRAST AGENT IMAGING WITH DESTRUCTION PULSES IN DIAGNOSTIC MEDICAL ULTRASOUND

(75) Inventors: Sriram Krishnan, San Jose; Gregory L. Holley, Mountain View; Edward A. Gardner, San Jose; Samuel H. Maslak, Woodside, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/348,246

(22) Filed: Jul. 2, 1999

(51) Int. Cl.$^7$ ................................................. A61B 8/00
(52) U.S. Cl. ...................................... 600/447; 600/458
(58) Field of Search ................................ 600/440–441, 600/443, 447, 458; 73/625–626

(56) References Cited

U.S. PATENT DOCUMENTS

| | | |
|---|---|---|
| 4,689,986 A | 9/1987 | Carson et al. |
| 5,219,401 A | 6/1993 | Cathignol et al. |
| 5,233,994 A | 8/1993 | Shmulewitz |
| 5,255,683 A | 10/1993 | Monagham ............ 128/662.02 |
| 5,456,257 A | 10/1995 | Johnson et al. ........ 128/662.02 |
| 5,560,364 A | 10/1996 | Porter ................... 128/662.02 |

(List continued on next page.)

FOREIGN PATENT DOCUMENTS

| | | |
|---|---|---|
| GB | 9901270.0 | 1/1999 |
| WO | WO 98/32378 | 7/1998 |
| WO | WO 99/35967 | 7/1999 |

OTHER PUBLICATIONS

"Multi–Pulse Ultrasound Contrast Imaging Based on A Decorrelation Detection Strategy" Frinking et al.; 1998 IEEE Ultrasonics Symposium.

"A New Multi–Pulse and Decorrelation–Detection Strategy For Improved Ultrasound Contrast Imaging" Frinking et al.; 4th Thoraxcenter European Symposium on Ultrasound Contrast Imaging (Jan. 21–22, 1999).

(List continued on next page.)

*Primary Examiner*—Francis J. Jaworski
(74) *Attorney, Agent, or Firm*—Brinks Hofer Gilson & Lione

(57) ABSTRACT

The invention is directed to improvements in diagnostic medical ultrasound contrast agent imaging. In a preferred embodiment, high pulse repetition frequency (HPRF) destruction pulses are fired at a rate higher than necessary for receiving returning echoes. Pulse parameters can also be changed between the plurality of contrast agent-destroying pulses. Other preferred embodiments of the invention are directed to simultaneous transmission of multiple beams of destruction pulses. Destruction frames that consist of a plurality of destruction pulses can be triggered and swept over the entire region of tissue being imaged and at a variety of focal depths from the transmitter. The destruction frames are fired at some time triggered from a timer or some fixed part of a physiological signal, such as an ECG signal. Other preferred embodiments of the invention are directed to continuous low power imaging pulses alternating with destruction pulses triggered at a fixed point of a physiological signal, and a comparison of the received signals from imaging pulses fired before and after the destruction pulses. Alternatively, destruction pulses are triggered at a fixed point on a physiological signal different from the fixed point of a physiological signal used to trigger imaging pulses. In another embodiment, triggered destruction frames are used to enable a comparison of imaging frames in order to determine physiological functions, such as perfusion of blood in cardiac tissue. Finally, in another embodiment, destruction pulses are combined with subharmonic imaging.

121 Claims, 7 Drawing Sheets

U.S. PATENT DOCUMENTS

| | | |
|---|---|---|
| 5,581,517 A | 12/1996 | Gee et al. .................... 367/138 |
| 5,675,554 A | 10/1997 | Cole et al. ................... 367/138 |
| 5,685,308 A | 11/1997 | Wright et al. ........... 128/662.07 |
| 5,685,310 A | 11/1997 | Porter ................... 128/662.02 |
| 5,694,936 A | 12/1997 | Fujimoto et al. |
| 5,694,937 A | 12/1997 | Kamiyama ............. 128/661.01 |
| 5,735,281 A | 4/1998 | Rafter et al. ........... 128/662.02 |
| 5,827,188 A | 10/1998 | Wright et al. ................ 600/447 |
| 5,833,614 A | 11/1998 | Dodd et al. |
| 5,833,615 A | 11/1998 | Wu et al. |
| 5,883,613 A | 11/1998 | Averkiou et al. ........... 600/440 |
| 5,856,955 A | 1/1999 | Cole et al. ................... 367/138 |
| 5,860,931 A | 1/1999 | Chandler |
| 5,882,307 A | 3/1999 | Wright et al. ............... 600/442 |
| 5,935,069 A | 8/1999 | Chandler et al. |
| 5,944,666 A | 8/1999 | Hossack et al. |
| 5,947,904 A | 9/1999 | Hossack et al. |
| 5,957,845 A | 9/1999 | Holley et al. |
| 5,961,464 A | 10/1999 | Poland |
| 5,971,928 A | 10/1999 | Dodd et al. |
| 6,080,107 A | 6/2000 | Poland |
| 6,104,670 A | 8/2000 | Hossack et al. |
| 6,108,572 A | 8/2000 | Panda et al. |
| 6,171,246 B1 * | 1/2001 | Averkiou et al. ........... 600/458 |

OTHER PUBLICATIONS

"Characteristic Signature Effects of Gas–Containing Micro–bubbles by Use of Ultrasound", *Mads Haugbro*, Sivilingenior (MSc) Thesis, Norwegian University of Science and Technology, Department of Engineering Cybernetics, Oslo, Dec. 1996.

"Quantification of Myocardial Blood Flow With Ultrasound–Induced Destruction of Microbubbles Administered as a Constant Venous Infusion". Kevin Wei, MD, et al. (*Circulation*, 1998;97 pp. 473–483).

"Harmonic Power Mode Doppler Using Microbubble Contrast Agents: An Imporved Method for Small Vessel Flow Imaging". P. N. Burns, et al. 1994 IEEE Ultrasonics Symposium, pp. 1547–1550.

* cited by examiner

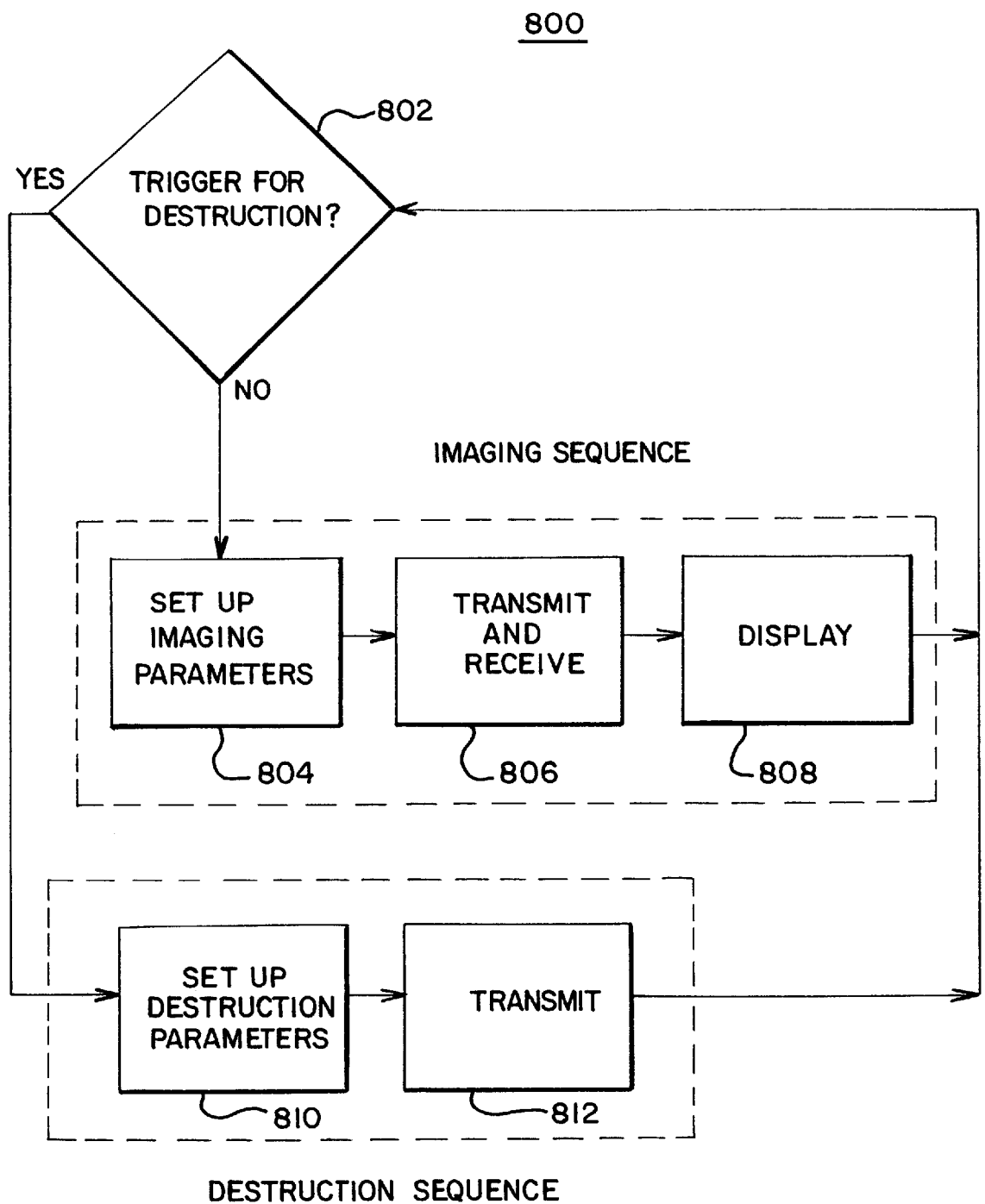

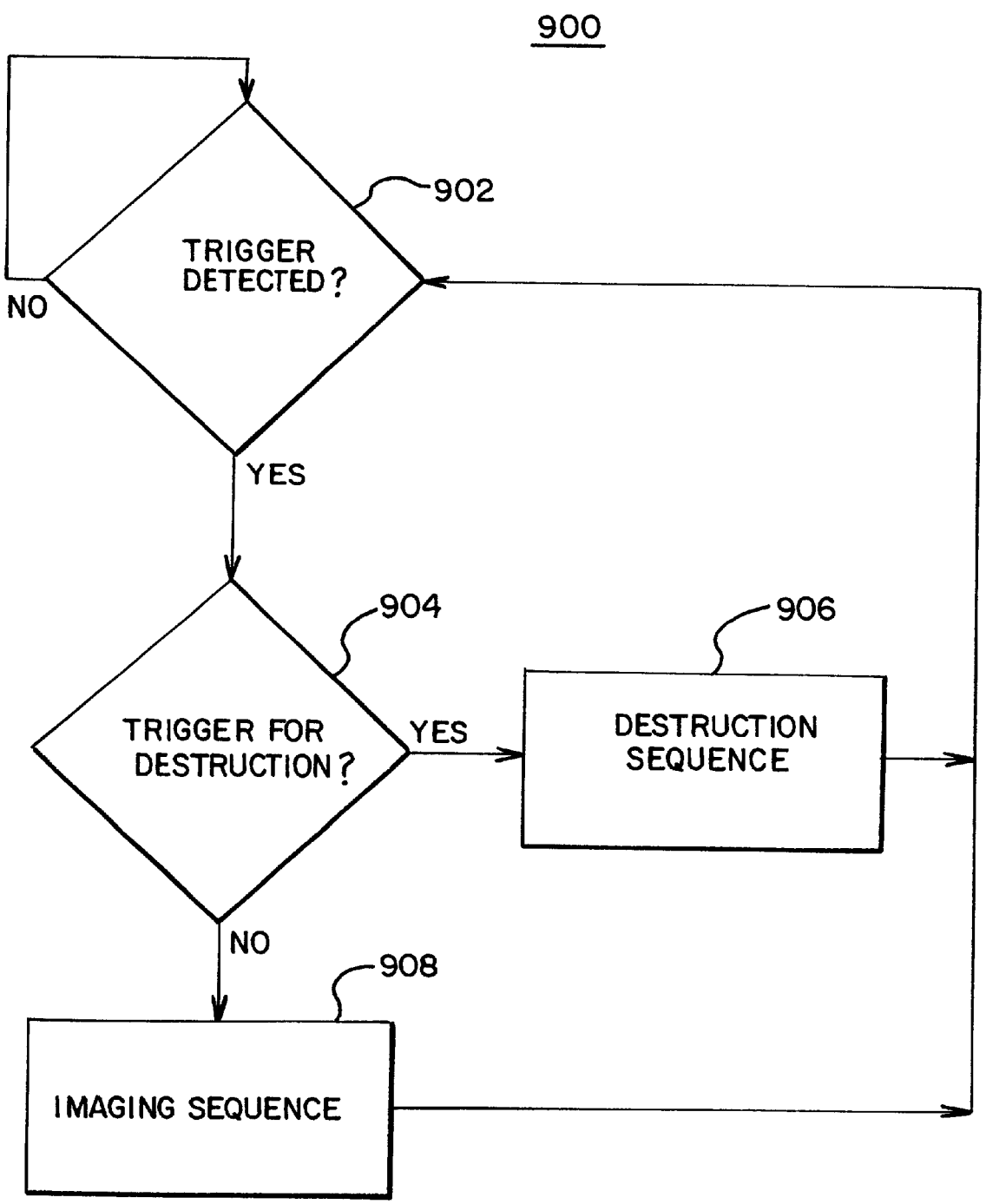

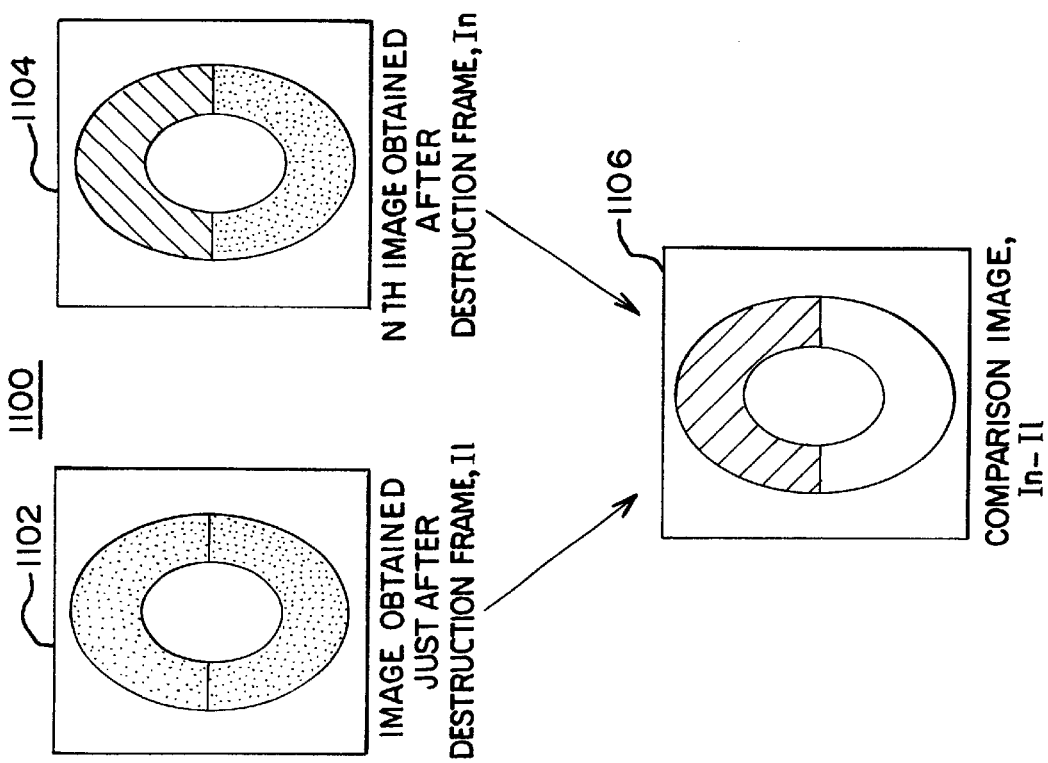
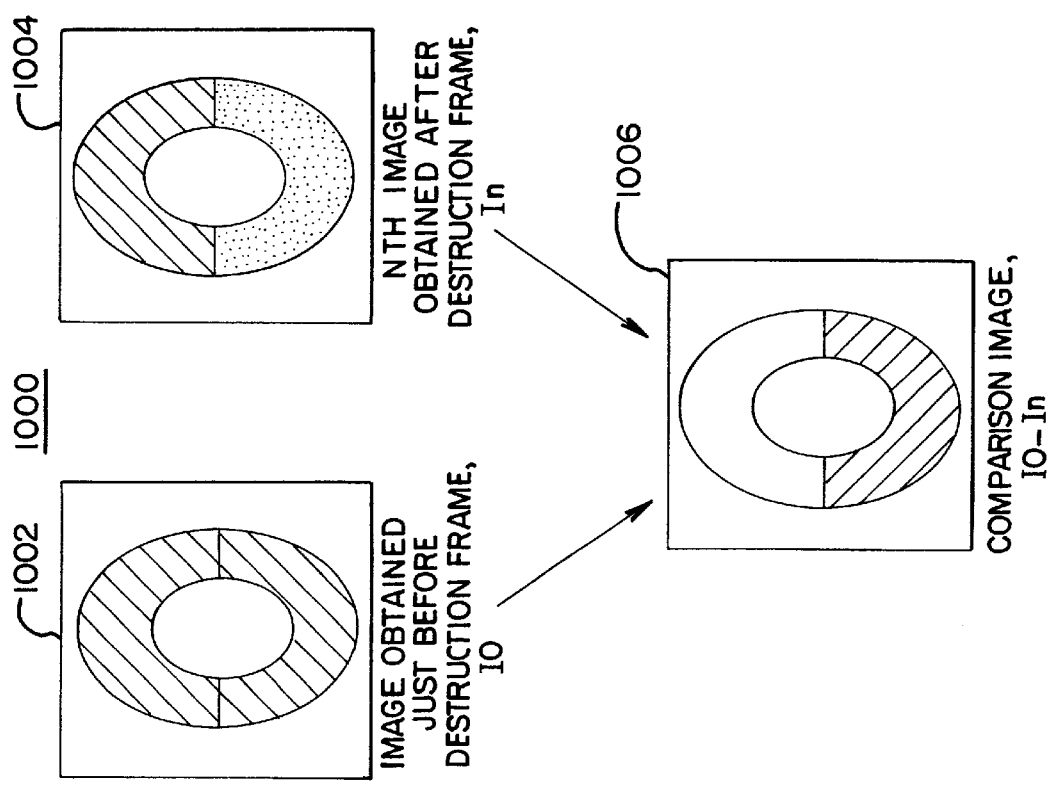

CONTRAST AGENT IMAGING WITH DESTRUCTION PULSES IN DIAGNOSTIC MEDICAL ULTRASOUND

BACKGROUND OF THE INVENTION

1. Field of Invention

This invention relates generally to an improvement in diagnostic medical ultrasound imaging, and more specifically to more effective medical imaging of a human or animal due to improved utilization of an ultrasound contrast agent.

2. Description of the Prior Art

A major goal of contrast agent imaging in diagnostic medical ultrasound is the measurement of physiological functions, such as perfusion of blood into tissue, by measuring the flow of contrast agent into tissue. In order to accomplish this, it is important to differentiate contrast agent from tissue.

One method for achieving the differentiation of contrast agent and tissue is the loss-of-correlation (LOC) method in which multiple pulses are fired into a body containing contrast agent. The first pulse produces a return signal from both contrast agent and tissue, and simultaneously destroys contrast agent. Since contrast agent is destroyed, the second pulse produces relatively more signal from tissue. By subtracting the two signals, the signal from the contrast agent is enhanced; while the signal from tissue, which is in both pulses, is suppressed. The two pulses can be acquired in the same frame (e.g. color Doppler processing) or in different frames. The more contrast agent that is destroyed between firings, the better the differentiation between contrast agent and tissue.

This method has drawbacks. First, a single pulse will rarely destroy all the contrast agent along a given ultrasound line. As a result, many pulses are needed to destroy the contrast agent. Firing many pulses along the same line will reduce the system frame rate, and thereby increase motion artifacts due to tissue motion, especially in cardiac applications. The system frame rate is defined as the actual frame rate at which images can be obtained by the ultrasound system. Secondly, the pulses which best destroy contrast agent are low frequency, long duration (low bandwidth) pulses. However, for better imaging resolution, high frequency, short duration (high bandwidth) pulses are needed. For second harmonic imaging, low frequency pulses are used, but these pulses are still short duration in order to provide good imaging resolution. Usually, a compromise is made between the requirements for imaging and destruction of contrast agent, further reducing the efficiency of contrast agent destruction by ultrasound pulses.

Another approach to LOC imaging, which overcomes this compromise, is to generate two types of pulses, one type for imaging and one type for destroying contrast agent. For example, a transmitter sends an imaging pulse into a region of interest in a body, followed by a pulse for destruction of contrast agent. A second imaging pulse is then sent into the region of interest in the body and the two images of the region before and after contrast agent destruction are compared.

However, this does not overcome the system frame rate problem, but in fact may make it worse. Furthermore, this approach to LOC imaging does not allow contrast agent to perfuse into a region of interest between firings of pulses for destroying contrast agent, so there is little contrast agent to image after destruction. Contrast agent perfusion imaging requires sending the pulses for destroying contrast agent only at specific intervals. Still further, a single pulse will rarely destroy all the contrast agent along a given ultrasound line.

Another approach discussed in the prior art is to use high power pulses simultaneously for imaging and destruction. In this case, low power pulses, or "locator frames" are used to image the body, and then at times determined by a timer or an ECG signal, a high power signal is sent to image the contrast agent as well as destroy it. The problem with this approach is that the same high power pulses are simultaneously used to both image and destroy the contrast agent. Therefore, trade-offs in the pulse parameters are made based on the desired amount of destruction, spatial resolution, and desired system frame rate.

Therefore, it would be desirable to improve the LOC method by enhancing the difference between contrast agent and tissue, without sacrificing the system frame rate or imaging resolution. Furthermore, an improved method for measuring physiology, such as perfusion, is needed.

SUMMARY OF THE INVENTION

One object of the invention is to enhance the difference between contrast agent and tissue without sacrificing the system frame rate or imaging resolution.

Another object of the invention is to improve the efficiency of contrast agent destruction.

Another object of the invention is to provide a better method for measuring and/or displaying physiology, such as perfusion.

A first aspect of the invention is directed to destroying contrast agent by use of high pulse repetition frequency (HPRF) destruction pulses. These pulses are transmitted at a rate faster than required to allow the pulses to propagate to the farthest boundary of the region of interest being imaged and return to the transducer.

A second aspect of the invention is directed to transmitting multiple destruction beams simultaneously in different directions to destroy contrast agent quickly over a region.

A third aspect of the invention is directed to triggering destruction frames at a fixed point of a physiological signal (e.g., every n beats of a cardiac cycle, where n is an integer), and displaying continuous imaging frames between the destruction frames.

A fourth aspect of the invention is directed to triggering destruction frames at a fixed point of a physiological signal, and displaying, between the destruction frames, imaging frames that are triggered at a different fixed point of the physiological signal.

A fifth aspect of the invention is directed to using triggered destruction frames and imaging frames and comparing imaging frames.

A sixth aspect of this invention relates to combining destruction pulses with subharmonic imaging.

These and other objects and advantages of the invention will become apparent to those skilled in the art from the following detailed description of the invention and the accompanying drawings.

BRIEF DESCRIPTION OF THE DRAWINGS

FIG. 8 shows a flow chart explaining one mode of operation of the system controller of FIG. 5.

FIG. 9 shows a flow chart explaining another mode of operation of the system controller of FIG. 5.

FIG. 10 is a comparison of an image obtained just before a destruction frame and an image obtained just after a destruction frame.

FIG. 11 is a comparison of an image obtained just after a destruction frame and an image obtained from an nth imaging frame after the destruction frame.

DETAILED DESCRIPTION OF PREFERRED EMBODIMENTS OF THE INVENTION

Figure 1:
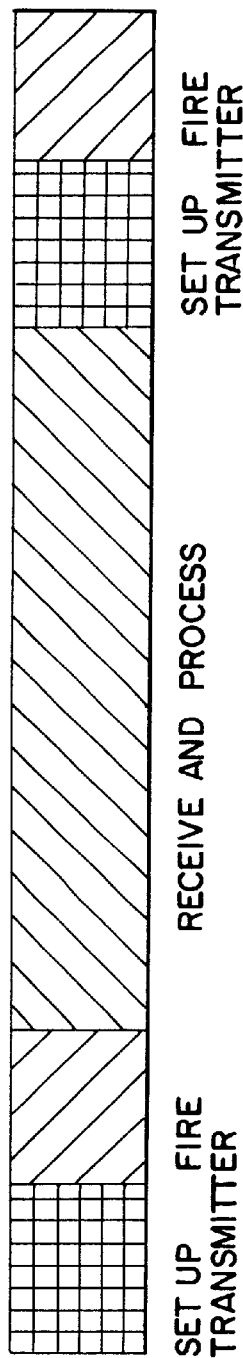
FIG. 1 shows a timing diagram of a normal imaging situation.

Imaging pulses are pulses which are transmitted, received, processed and displayed. Imaging pulses in some cases can also be destructive to contrast agent. On the other hand, destruction pulses are herein defined as pulses which are transmitted into a body, but not used for imaging. Since destruction pulses are not used for imaging, there is no need to optimize destruction pulse parameters for imaging. These destruction pulses can be optimized for destruction of contrast agent by using low frequency, low bandwidth and high power pulses.

The first aspect of the invention is directed to improving the efficiency of destruction of contrast agent by using high pulse repetition frequency (HPRF) destruction pulses. Here, HPRF destruction pulses are defined as pulses which are transmitted at a rate faster than required to allow the pulses to propagate to the farthest boundary of a region of interest and return to the transducer. Since destruction pulses are not processed or displayed, it is not necessary to wait for the ultrasound signal to propagate to the farthest boundary of a region of interest being imaged and for signals from deep tissue interfaces to return to the transducer. Rather, multiple pulses are fired very rapidly into the body. Accordingly, in the preferred embodiment of the invention, the pulse repetition frequency (PRF) can be as high as allowed by the ability of the transmitter to reset and transmit another pulse after a pulse has been fired.

Multiple destruction pulses are normally needed to adequately destroy contrast agent in the body. Conventional systems transmit at a pulse repetition interval sufficient to allow the transmitted pulse to travel to the farthest boundary of a region of interest being imaged and return to the transducer, as well as to allow time for any reverberations of the pulse to die out. For example, if a system is being used to image 100 mm in depth, then in order to allow the ultrasound to travel 100 mm and return to the transducer, assuming a speed of sound of 1.54 mm/microsecond (us), the transmitter must wait about 130 us between transmitter firings (ignoring the time for the reverberations to die out). If four pulses are needed to destroy the contrast agent along one line, then the system must wait 390 us to destroy all the contrast agent along that line. This represents a significant problem if there is significant tissue motion during that time interval. However, destruction pulses do not have to be received and processed; their only purpose is to destroy the contrast agent. Therefore, instead of waiting 130 us between firings, pulses can be fired at a more rapid rate. Preferably, these pulses are fired at the maximum rate allowed by the transmitter. For example, if it requires 10 us to reset a transmitter after firing, then 4 pulses can be fired along one line in only 30 us, rather than 390 us. This represents a significant improvement in the time it takes to destroy contrast agent in the body. Of course, one can practice this invention by transmitting at any PRF faster than required to receive echoes from the farthest boundary of a region of interest, in this example, at any interval between 10 us and 130 us. However, at very shallow depths, HPRF pulses are less advantageous because the transmitter reset time is a large fraction of the pulse propagation time.

Figure 2:
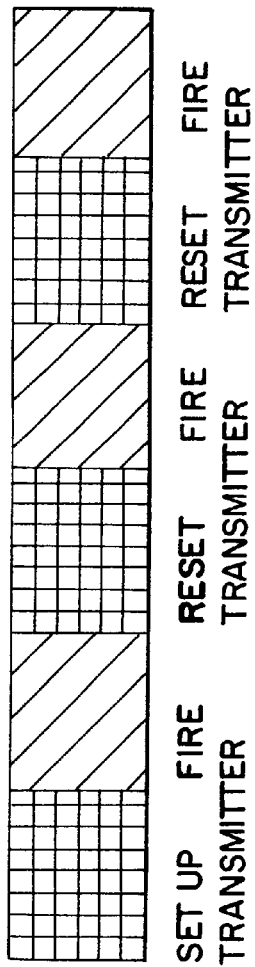
FIG. 2 shows an HPRF timing diagram.

FIGS. 1 and 2 show simple timing diagrams for an example illustrating the difference between normal pulse transmission and HPRF pulse transmission. The timing diagrams depict the timing of actions for a transmitter and receiver. FIG. 1 shows a normal imaging situation. First the transmitter is set up, then a pulse is transmitted. Then the receiver waits for the received signals and processes them, before the whole sequence is repeated. FIG. 2 shows an HPRF timing diagram. In this example, the transmitter is set up, and then a destruction pulse is fired. The transmitter is then reset and another destruction pulse is fired. There is no pause to receive and process the returning signals, since only destruction is intended.

Another improvement can be made to HPRF destruction pulses to increase the efficiency of destruction by changing pulse parameters between the multiple firings of HPRF destruction pulses. For example, a maximum number of bubbles of contrast agent are destroyed at the point of peak intensity, which is very close to the transmit focus. In a preferred embodiment, the transmit focus is changed between successive pulse firings to uniformly destroy all the contrast agent along a given line.

For example, in order to destroy all the contrast agent along a given line, the system begins by firing one or more destruction pulses focused at a first depth. The focal depth is then changed, and mutiple pulses fired at a second depth. Optionally, the focal depth is then changed further, and one or more pulses are fired at one or more additional depths. In the preferred embodiment of the invention, this sequence is then repeated for several ultrasound lines covering a region. An alternative method involves firing one or more pulses focused at one depth for all the lines. Then, the focal depth is changed, and one or more pulses focused at this new depth are fired for all the lines, and this step is repeated as necessary.

Other parameters, such as transmit frequency, can also be varied to achieve substantial destruction along a line. Transmit frequency is important because lower frequency pulses have less attenuation and are able to penetrate deeper into the body. Moreover, destruction pulses can be fired at various frequencies in sequence to increase the efficiency of contrast agent bubble destruction. Since a population of bubbles consists of bubbles of varying sizes, which will preferentially burst at different resonating frequencies, destruction with pulses of different frequencies increases the efficiency of bubble destruction.

Pulse power can also be increased for better destruction coverage throughout the field of view. For example, different destruction beams focused at different focal depths can have different transmitted power levels, such that destruction beams focused at deeper depths are fired at a greater transmitted power level than destruction beams focused at shallower depths to achieve uniform destruction along a line. The government regulatory (e.g., the Food and Drug Administration) limits on transmit pulse power and the benefits of using a maximum amount of power are discussed more filly in co-pending U.S. Pat. No. 6,045,506, entitled "Ultrasonic Imaging Method and Apparatus for Adjusting Transmitted Power Levels," filed on Aug. 31, 1998, which is assigned to the assignee of the present invention and hereby incorporated by reference. The teachings and advantages disclosed therein can be combined with any aspect of this invention. Accordingly, transmit power can also be varied as a function of angle from the center of the array; or as a combination of depth and such lateral angle.

In a second aspect of the invention, multiple transmit beam techniques are used to increase the speed and efficiency of contrast agent destruction without a reduction in the system frame rate. Cole, et al. disclose an ultrasound system capable of transmitting multiple beams in different directions simultaneously in U.S. Pat. No. 5,675,554. Other ultrasound systems capable of firing multiple beams may also be used with this invention.

Figure 3:
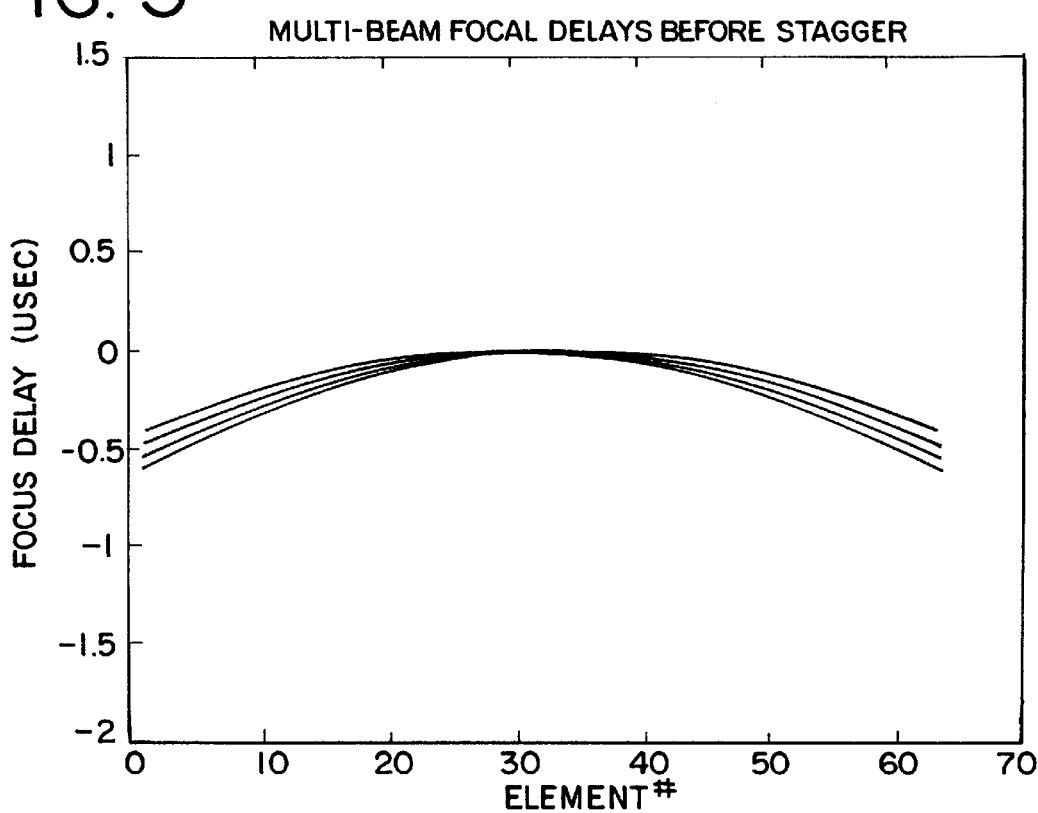
FIG. 3 shows focusing delay profiles for four beams without beam stagger.

In one embodiment of the invention, several closely spaced beams are sent out simultaneously. Preferably, the beams are staggered so that the different beams do not overlap as they are transmitted. FIG. 3 shows focusing delay profiles for four beams without beam stagger. In this example, the focusing delays shown are for closely spaced beams steered at slightly different angles about the center of the array. Here, negative numbers represent advance (pulses are transmitted earlier) and positive numbers represent delay (pulses are transmitted later). As shown, the delay curves cross over each other, indicating that pulses for the different beams are transmitted at the same time from some element. In this case, the pulse at that element is the superposition of the pulses required for each beam. This can increase the peak amplitude required to transmit the multiple beams correctly; and because a transmit beamformer typically has a maximum peak transmit amplitude, either the amplitude of all four beams must be decreased, or the transmit signal for some elements will be saturated. Furthermore, ultrasound pulses have a finite duration, so that interference and subsequent signal strength limitation can occur even if the pulses do not exactly overlap.

Figure 4:
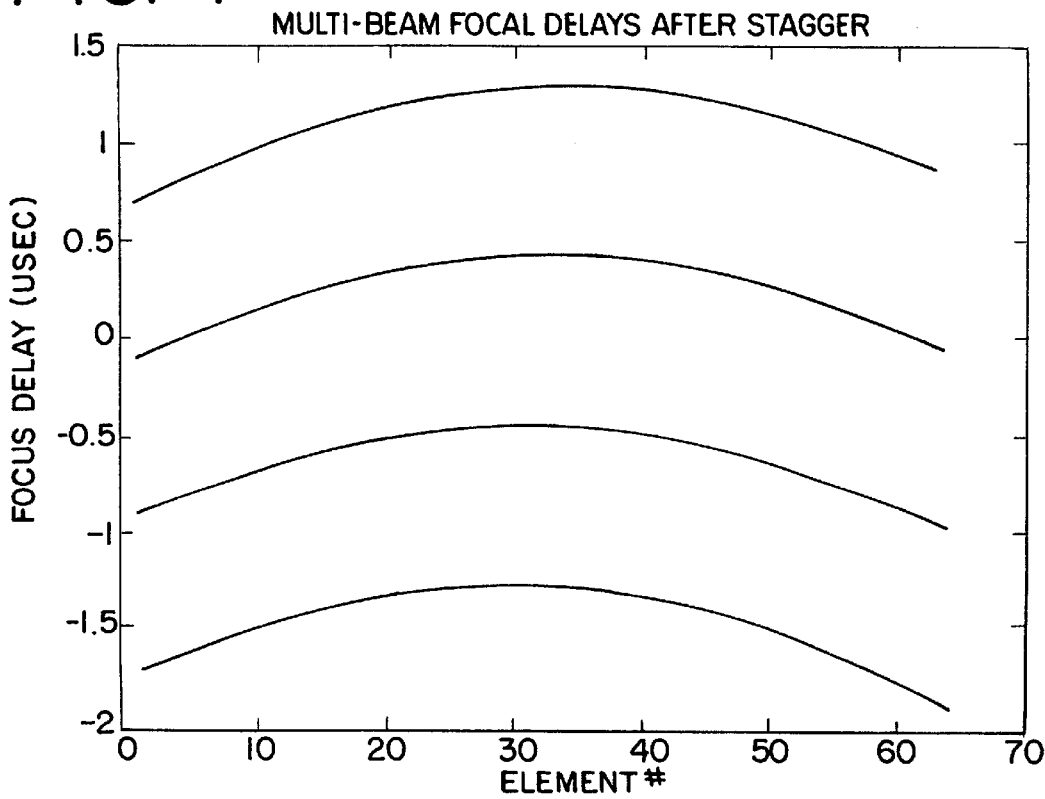
FIG. 4 shows an example of using beam stagger in the preferred embodiment.

FIG. 4 shows an example of using beam stagger in the preferred embodiment. Here, a delay of slightly more than 0.8 us was added in between each set of adjacent beams. This enables the four beams to be transmitted without interference at the transducer. Hence all four beams can be transmitted without reducing the transmit amplitude and without incurring saturation at some transmitter elements.

Of course, beneficial results can also be obtained using this aspect of the invention (the use of multiple transmit beams with destruction pulses) without beam stagger. Because the destruction pulses are not used for imaging, a level of saturation or interference between the beams may be tolerated which is not acceptable in a prior art diagnostic medical ultrasound imaging system.

While the example described above was directed to closely spaced multiple transmit beams, this aspect of the invention can also be practiced with widely spaced multiple transmit beams.

In an alternate embodiment, multiple beam transmit technology is used to implement either HPRF destruction pulses and/or to vary pulse parameters between destruction pulses fired along the same line. For example, a sequence of two or more identical pulses is fired in the same direction, staggered as described above, while the receive beamformer is disabled. This allows destruction pulses to be fired at an extremely high rate, as the transmit beamformer does not need to be reset between every firing. In addition, on some beamformers, the invention may be easier to implement this way than by changing the sequence and repetition frequency of pulse firing. Alternatively, the pulses fired in the same line are focused at different depths, and again, are preferably staggered to prevent overlap.

A third aspect of the invention is directed to triggering destruction frames and displaying continuous imaging frames between the destruction frames. Here, continuous imaging frames are defined as imaging frames that are fired one after the other, with only enough time between frames for the last pulse of the previous frame to propagate to the farthest boundary of the region imaged and return to the transducer, with some overhead for the system to complete the frame. This overhead time between frames includes time for the system to remove any reverberations, process and display the image, and complete one imaging frame before beginning another imaging frame. A destruction frame consists of a series of destruction pulses, preferably swept over the entire field of view and at a variety of focal depths in order to achieve uniformity of contrast agent destruction throughout the field of view. A HPRF destruction frame consists of a series of HPRF destruction pulses. Triggered destruction frames are destruction frames fired at some time triggered from a timer or physiological signal, such as a cardiac signal (e.g., an ECG signal) or a respiratory signal. Triggering can occur at some fixed or variable time after the physiological signal. Triggered destruction frames are alternated with imaging frames fired in a continuous mode.

A fourth aspect of the invention is directed to triggering destruction frames at a fixed point of a physiological signal and displaying, between the destruction frames, imaging frames that are triggered at a different fixed point of the physiological signal.

A preferred embodiment provides a user interface that gives the operator the option of choosing either the third or fourth aspect of the invention. Therefore, destruction frames are triggered at a fixed point of a physiological signal (e.g., every n beats of a cardiac cycle or respiratory cycle, where n is an integer), and between the destruction frames, either continuous imaging frames are displayed, or imaging frames are displayed that are triggered at a different time (e.g., every m beats of a cardiac cycle or respiratory cycle, where m is an integer) than the destruction frames. For example, the imaging frames can be triggered at the same point of the cardiac cycle, but in a different cardiac cycle than the destruction frames. Alternatively, the imaging frames can be triggered at a different point in the cardiac cycle, in the same cardiac cycle(s) as or different cardiac cycle(s) than the destruction frames.

Ideally, different aspects of the invention are combined. For example, HPRF destruction frames are combined with firing at different transmit foci and using multiple transmit beams to further improve the efficiency of the contrast agent destruction.

Figure 5:
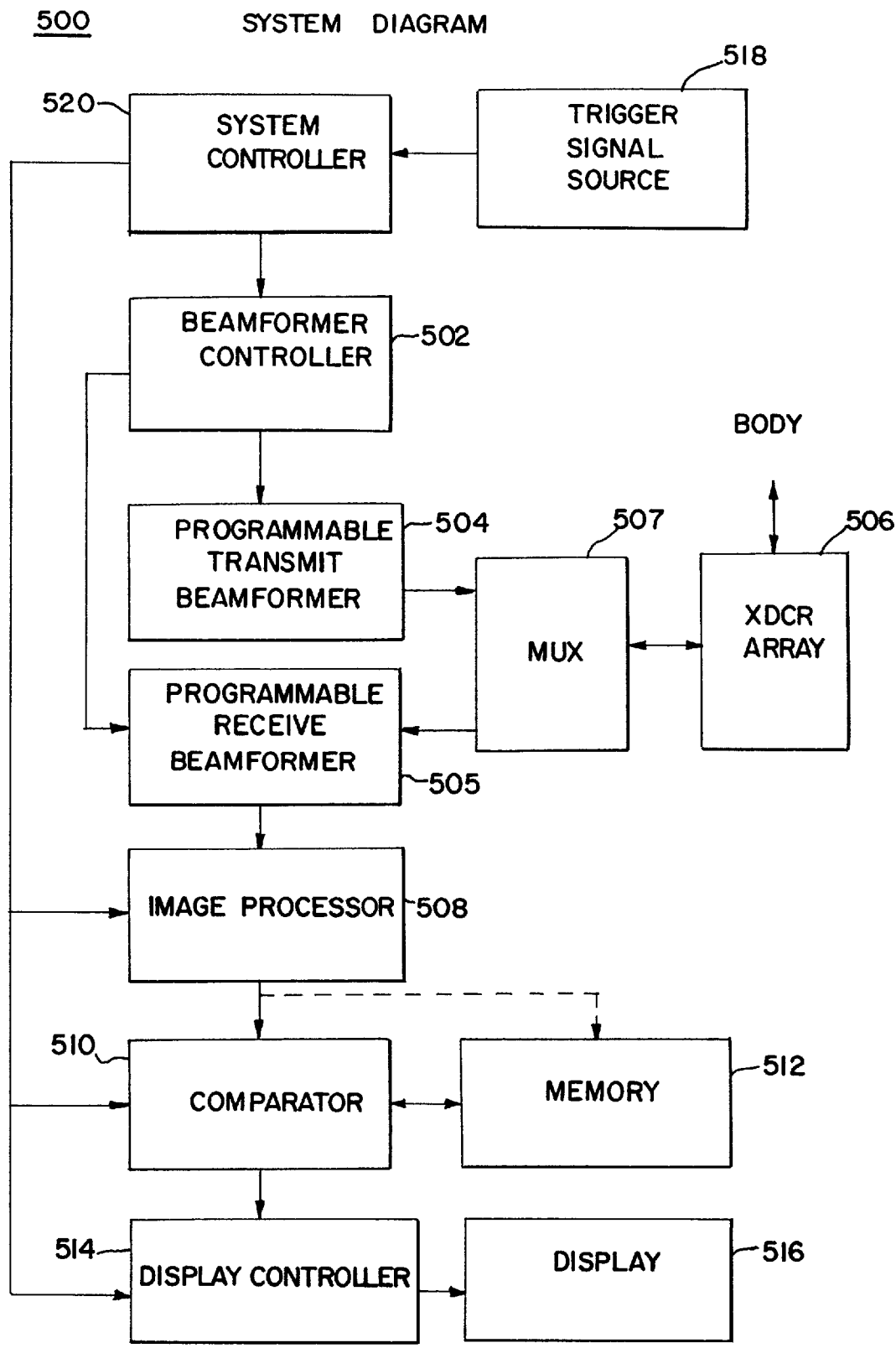
FIG. 5 is a block system diagram of a preferred embodiment for carrying out the invention.

FIG. 5 provides a schematic diagram of an ultrasound system 500 that incorporates a preferred embodiment of the invention. Ultrasound system 500 preferably includes programmable transmit beamformer 504 and receive beamformer 505 coupled to ultrasonic transducer 506 via multiplexer 507. Disclosures of such beamformers are available: for example, receive beamformers are described in U.S. Pat.

Nos. 5,685,308, 5,882,307, and 5,827,188 to Wright, et al.; and transmit beamformers are described in U.S. Pat. Nos. 5,856,955 and 5,675,554 to Cole, et al., but other beamformers in the art can be used. Transmit and receive parameters are fed to beamformers 504 and 505 by beamformer controller 502, such as, but not limited to, that described in U.S. Pat. No. 5,581,517 to Gee, et al. Beamformer controller 502 controls beamforming parameters, such as transmit center frequency and bandwidth, receive center frequency and bandwidth, transmit power, receive gain, pulse repetition timing and transmit line spacing interval. Preferably, transmit beamformer 504 is also capable of transmitting multiple beams simultaneously in different directions. Transducer 506 comprises a phased array of transducer elements in one of various formats, such as a linear, curvilinear, one-dimensional, 1.5-dimensional, and two-dimensional array. Transmit beamformer 504 provides transmit waveforms to transducer 506, causing transducer 506 to emit ultrasonic pulses into the body, which contains both tissue and contrast agent scatterers. Ultrasound pulse scattering from the scatterers in the body returns ultrasound pulses to transducer 506, which sends signal waveforms to receive beamformer 505 via the multiplexer 507. The multiplexer 507 contains a transmit/receive switch which can switch between transmit and receive states for imaging pulses, but which will otherwise remain in the transmit state for destruction pulses. Receive beamformer 505 may optionally take the received signal waveforms and form outputs, which can be passed on to display controller 514 and display 516 (typically via image processor 508 and optionally through comparator 510). Image processor 508 provides signal processing of the signals generated from receive beamformer 505, and optionally provides input data to comparator 510 and memory 512. Alternatively, image processor 508 can be integrated with comparator 510 and/or display controller 514. Before going to display controller 514, the signals from image processor 508 preferably pass through comparator 510, which can compare the signals to previous stored signals in memory 512. Display controller 514 then prepares the signals for display, e.g., by scan conversion and other processing known in the art. Display controller 514 optionally also superimposes the output of comparator 510 on a conventional B-mode image, harmonic B-mode image, color Doppler image, tissue Doppler image, pulse inversion B-mode image, or pulse inversion Doppler image. The output of comparator 510 can alternatively be displayed in graphical or tabular form. System controller 520 controls beamformer controller 502, image processor 508, and display controller 514. It also controls comparator 510, allowing optional different comparisons to be calculated and passed on display controller 514. Trigger signal source 518 is responsive to physiological signals (e.g., respiratory signals, or ECG signals supplied by an ECG device, not shown) or to internal or external timers (not shown). Trigger signal source 518 preferably includes conventional hardware or software which recognizes some portion of a physiological signal (e.g., the R-wave of an ECG signal) and generates a trigger signal based thereon. Alternatively, trigger signal source 518 can be activated by an internal timer or an external timer.

Preferably, the images created and displayed by the ultrasound system are any type of image which shows contrast agent. In carrying out the invention, any type of ultrasound data can be used, alone or in combination. Specifically, any of the following ultrasound imaging modalities can be used in accordance with the embodiments taught herein, with either fundamental, harmonic, or subharmonic imaging or a combination thereof: B-mode, Color Doppler Velocity, Color Doppler Energy, Color Doppler Variance, Doppler Tissue Velocity, Doppler Tissue Energy, Doppler Tissue Acceleration, pulse inversion B-mode, pulse inversion Doppler, or any combination thereof. Alternatively, B-mode images are acquired by using alternating line technology, such as alternating line phase (ALP), as described in a co-pending U.S. patent application Ser. No. 09/282,396, entitled "Diagnostic Ultrasound Imaging Method and System with Improved Frame Rate," filed Mar. 31, 1999, assigned to the assignee of the present invention and hereby incorporated by reference. All of these imaging modes can be carried out in a variety of ways. For example, in color Doppler modes and B-mode, data can be acquired and interleaved by line, block (i.e., a group of lines less than a frame), or frame. Of these methods, B-mode harmonic imaging, subharmonic imaging, ALP, and pulse inversion imaging are preferred because of their ability for non-linear detection of contrast agent, as well as for their ability to work at low power, where contrast agent is not destroyed.

Figure 6:
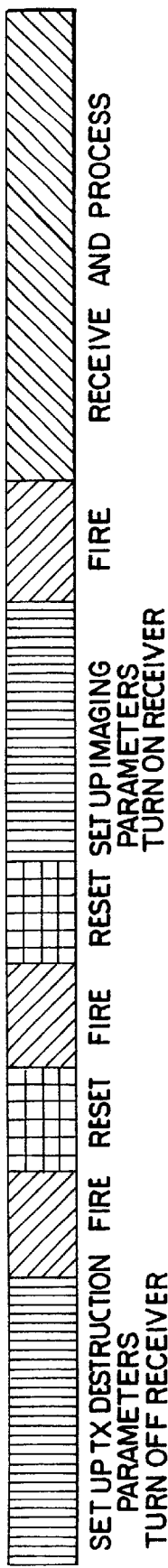
FIG. 6 shows a timing diagram describing how the system of FIG. 5 implements a simple sequence of two destruction pulses followed by an imaging sequence.

FIG. 6 shows a timing diagram illustrating how ultrasound system 500 of FIG. 5 implements a simple sequence of two destruction pulses followed by an imaging sequence. First, transmit beamformer 504 is programmed by beamform controller 502 with parameters to transmit destruction pulses, and receive beamformer 505 is turned off. Transmit beamformer 504 then fires the destruction pulses, and resets itself. In this case, a second destruction pulse is then fired, and transmit beamformer 504 is reset. Next, beamform controller 502 programs imaging parameters for transmit beamformer 504, and receive beamformer 505 is turned on to receive and process the returning data. Transmit beamformer 504 is then fired, and receive beamformer 505 receives and processes the received data. This entire sequence is optionally controlled by system controller 520.

In this case, different parameters are used to set up the imaging and destruction pulses. For example, if ultrasonic transducer 506 has an overall bandwidth from 1.5 to 4 MHz, then beamformer controller 502 sets up ultrasound system 500 for imaging using low power harmonic B-mode imaging. In this case, ultrasound system 500 is set up for a transmit frequency of 1.75 MHz, a transmit pulse with a Gaussian envelope having a 6 dB fractional bandwidth of 33%–50%, and a transmit power corresponding to a mechanical index (MI) of 0.4. Other transmit and receive parameters, such as transmit foci, receive filters, etc., are set properly for harmonic imaging. An example for destruction pulses is ultrasound system 500 set up for a transmit frequency of 1.75 MHz, a transmit pulse with a rectangular envelope having a 6 dB fractional bandwidth of 10%, and a transmit power corresponding to a MI of 1.9. These parameters are one example of a system set up for destruction of contrast agent. The use of the MI parameter incorporates both the pressure and the frequency dependence of pulses used for contrast agent destruction.

Destruction pulses are transmitted at a pressure high enough to destroy contrast agent. The best transmit frequency to use is transducer dependent, and may also depend on the particular bubble population being destroyed. Also, in general, the longer the pulse length, the more destructive the pulse. Generally, destruction pulses have a MI greater than 0.6 to destroy contrast agent. Preferably, in order to destroy contrast agent, the MI is above 1.0. Most preferably, the MI is above 1.5.

Figure 7:
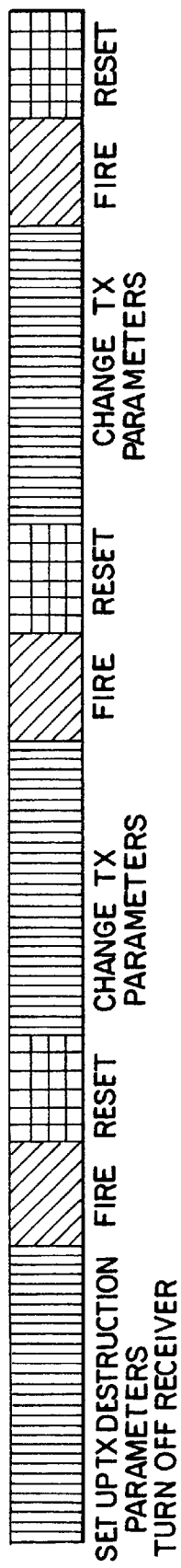
FIG. 7 shows a timing diagram describing how the system of FIG. 5 changes parameters between destruction pulses.

FIG. 7 shows a timing diagram illustrating how ultrasound system 500 of FIG. 5 changes parameters between destruction pulses. First, transmit beamformer 504 is programmed by beamformer controller 502 with parameters to fire destruction pulses, and receiver 505 is turned off. Transmit beamformer 504 then fires the destruction pulse, and resets itself. Next, the transmit parameters are changed. For instance, the transmit focus is set for a new depth. Then transmit beamformer 504 fires the destruction pulse with the new transmit parameters, and resets itself. And the sequence is repeated a third time. For example, three destruction pulses are fired with three different transmit focal depths. Again, this entire sequence is optionally controlled by system controller 520.

FIG. 8 shows a flow chart 800 for one mode of operation of system controller 520 of FIG. 5. This mode of operation provides continuous imaging, with destruction pulses either triggered from a timer or a physiological signal (e.g., an ECG signal or a respiratory signal). If triggered from an ECG signal, a destruction pulse sequence is fired once every n beats. In this mode, in step 802, system controller 520 tests for a trigger from trigger signal source 518. If no trigger is detected, ultrasound system 500 images continuously: system controller 520 controls beamformer controller 502 to set up the correct imaging parameters for imaging in step 804; sets up transmit beamformer 504, multiplexer 507, and receive beamformer 506 for transmit and receive in step 806; and sets up display controller 514 to display the image in step 808. When a trigger from trigger signal source 518 is detected from step 802, system controller 520 controls beamformer controller 502 to set up the pulse parameters for destruction in step 810, and sets up transmit beamformer 504 and multiplexer 507 for transmit only in step 812. Ultrasound system 500 then returns to the imaging mode until the next trigger in step 802.

Preferably, ultrasound system 500 images by using a non-destructive imaging mode, and the destruction of contrast agent is achieved by HPRF destruction frames. Most preferably, the imaging mode uses low power harmonic imaging, subharmonic imaging, pulse inversion, or ALP, with destruction of contrast agent achieved by using HPRF destruction frames with multiple transmit foci and multiple simultaneous transmit beams. Since the destruction pulses are fired in triggered mode, it is possible to fire higher power pulses than could otherwise be fired without triggering. This is because the power transmitted over a period of time can be averaged to satisfy governmental regulatory restrictions on ultrasound transmitter power.

FIG. 9 shows a flow chart 900 for another mode of operation of the system controller 520 of FIG. 5. This mode of operation provides triggered imaging, with destruction pulses triggered using a different trigger interval, either from a timer or a physiological signal (e.g., an ECG signal or a respiratory signal). In this mode, in step 902, system controller 520 tests for a trigger from trigger signal source 518. Once a trigger is detected, system controller 520 determines in step 904 if it is a destruction trigger or imaging trigger. If it is a destruction trigger, ultrasound system 500 executes a destruction sequence in step 906 as described above. If it is not a destruction trigger, and hence an imaging trigger, it executes the imaging sequence in step 908 described above. For example, high power color harmonic imaging could be used, which potentially could destroy some contrast agent. Destruction pulses could be used to destroy the remaining contrast agent.

There are several ways the mode of operation shown in FIG. 9 could be used. For example, an image could be acquired once every heartbeat, while a destructive pulse could be fired once every 5 heartbeats. Alternatively, the triggers for the imaging and destruction pulses could have the same timing interval, while being staggered by some number of heartbeats. For example, both the destruction frame and imaging frame could be fired every 5 heartbeats, but the destruction frame could be fired 3 heartbeats after each imaging frame. In yet another alternative, if the trigger intervals are varied, then re-flow is measurable for a variety of different time intervals. The preferred methods for destruction and imaging are the same as discussed above for FIG. 8.

A fifth aspect of the invention is directed to using triggered destruction frames and imaging frames and comparing imaging frames. Here, the act of comparing imaging frames can be performed either by the operator or by the ultrasound imaging system.

When the operator performs the act of comparing imaging frames, the ultrasound imaging system assists the operator in comparing the imaging frames. In one embodiment of the invention, the ultrasound imaging system displays two or more imaging frames side-by-side for the operator to visually compare the images to assess differences. Alternatively, the ultrasound imaging system tags two or more imaging frames and stores them in some image memory system, such as a frame buffer or video buffer, for example. When the tagged imaging frames are retrieved from the image memory system, the imaging frames can be visually placed next to each other, or a switch can allow the operator to quickly alternate the display of two or more imaging frames. In another embodiment of the invention, parameters derived from two or more imaging frames are displayed, for example in a graphical format.

In a preferred embodiment of the invention, the ultrasound imaging system compares two or more imaging frames and produces a new imaging frame which is a linear or non-linear combination of the imaging frames. The linear combination of the imaging frames can be as simple as addition or subtraction of two frames, or can be a weighted sum or difference. The system can also combine the frames in a non-linear fashion, e.g., by multiplying the two frames or by applying a non-linear function to a sum or difference of the two frames. Alternatively, any of the combinations can be presented as a graphical display of one or more parameters derived from comparing the imaging frames, such as the mean difference between two frames over a region of interest.

In another embodiment, the system can subtract the complex demodulated values associated with each pixel. In this case, the subtracted image is color coded and persisted over the continuous B-mode image. Alternatively, the amplitude or energy value associated with each pixel is subtracted, color coded, and persisted over the B-mode image.

Finally, more complicated means of comparison can be used. For example, the cross-correlation between the two images at each pixel or between complex demodulated values can be calculated and displayed. In this case, a fixed threshold can be used to distinguish LOC effects. Other on-line or off-line comparisons can also be used.

Prior to any comparison, the pixels on the imaging frames may be spatially or temporally filtered. For example, prior to making a comparison, pixels may be spatially averaged to reduce the effects of noise or speckle variations. Alternatively, pixels from different imaging frames may be temporally averaged to help reduce the effects of electronic noise. Such filtering may also improve the accuracy of parameter estimates derived from imaging frame comparison techniques.

FIG. 10 shows one type of comparison 1000 that can be made using the present invention. Here, the images are video inverted, so that contrast agent is dark and the absence of contrast agent is white. The upper left contains an image $I_0$ 1002 that been stored in memory just prior to a destruction sequence. Since image $I_0$ 1002 was acquired just before destruction, it is full of contrast agent and accordingly, appears to be relatively dark in the perfused regions. Let "$x_1$" be the complex demodulated value associated with each pixel in image $I_0$ 1002. The areas where contrast agent exists will have correspondingly high values of "$x_1$." Image $I_n$ 1004 on the upper right is the nth image obtained after destruction, and is accordingly much brighter in the unperfused region than in image $I_0$ 1002. Let "$x_2$" be the complex demodulated value associated with each pixel in image $I_n$ 1004. By subtracting the two complex demodulated values ("$x_1$"–"$x_2$"), a difference image 1006 can be created, shown in the lower part of FIG. 10. The value of each pixel of this difference image 1006 corresponds to the amount of contrast agent that has not returned by the time the nth image $I_n$ 1004 is obtained.

FIG. 11 shows another type of comparison 1100 that is carried out in a preferred embodiment of the present invention. Here, the images are video inverted, so that contrast agent is dark and the absence of contrast agent is white. The upper left contains an image $I_1$ 1102 that has been stored in memory immediately after a destruction sequence and accordingly, appears to be relatively bright. Since this image $I_1$ 1102 was acquired immediately after destruction, it is void or substantially void of contrast agent (i.e., at least about 70% and preferably at least 90% of the contrast agent was destroyed). Let "$x_1$" be the complex demodulated value associated with each pixel in image $I_1$ 1102. The image $I_n$ 1104 on the upper right is the nth image obtained after destruction, and is accordingly much darker in the perfused regions than in image $I_0$ 1102. Let "$x_2$" be the complex demodulated value associated with each pixel in image $I_n$ 1104. The areas where contrast agent exists will have correspondingly high values of "$x_2$." By subtracting the two complex demodulated values ("$x_2$"–"$x_1$"), a difference image 1106 can be created, shown in the lower part of FIG. 11. The value of each pixel of this difference image 1106 corresponds to the amount of contrast agent that has returned by the time the nth image $I_n$ 1104 is obtained.

Furthermore, parameters related to the rate of perfusion (i.e., the volume of fluid perfusion in a unit of time) can be estimated from these comparisons. For example, if one imaging frame is fired immediately after a destruction frame, and a second imaging frame is fired some time after the destruction frame, then the difference in signal levels between the two imaging frames indicates the amount of contrast agent that has perfused into a region over that time period. If the two imaging frames are subtracted, the signal level in the resultant difference frame would be equal to the amount of contrast agent that has perfused into the region. The rate of perfusion can then be estimated by the equation given below:

$$R = E/T \qquad (1)$$

where "R" is the linear approximation of the rate of perfusion, "E" is the amount of contrast agent that has perfused into a region over a time period, and "T" is the time period. In this case, the rate of perfusion estimate is normalized by the total amount of contrast agent that can exist in a unit volume of tissue.

If multiple measurements are made at different times after a destruction pulse, then more complex models can be used. For example, if multiple imaging frames, $I_1, I_2, \ldots I_n$, are acquired after a destruction frame at specific times, $T_1, T_2, \ldots T_n$, then the amount of contrast agent that has perfused into the region at each of these times can be estimated by subtracting the imaging frame immediately following the destruction frame from each of these imaging frames. The resulting difference frames, $F_1, F_2, \ldots F_n$, can then, on a pixel-by-pixel or region-by-region basis, provide data on the amount of contrast agent that has perfused. For example, the data could be fit into an exponential model of perfusion given below:

$$P = A\{1 - \exp(-Bt)\} \qquad (2)$$

where "P" is the estimated perfusion at time "t," and the values of "A" and "B" are curve-fitted to the data on the amount of contrast agent that has perfused into a region in the difference frames, $F_1, F_2, \ldots F_n$. In this way, perfusion can be measured as a function of time.

One approach for curve-fitting an exponential equation to measured values of the amount of contrast agent that has perfused into a region is described in the article "*Quantification of Myocardial Blood Flow With Ultrasound-Induced Destruction of Microbubbles Administered as a Constant Venous Infusion*," by K. Wei, et al., *Circulation*, Vol. 97, pp. 473–483 (1998), hereby incorporated by reference. Another approach is described in co-pending U.S. patent application Ser. No. 09/184,749, entitled "Ultrasonic System and Method for Imaging Subtraction," filed Nov. 2, 1998, assigned to the assignee of the present invention and hereby incorporated by reference.

Alternatively, one could subtract the multiple imaging frames, $I_1, I_2, \ldots I_n$, from an imaging frame immediately prior to the destruction frame. In this case, the resulting difference frames, $F_1, F_2, \ldots F_n$, represent the amount of contrast agent that has not yet reperfused into a region. In this case, the resulting difference frames, $F_1, F_2, \ldots F_n$, can provide data for curve-fitting the exponential equation given below:

$$Q = A \exp(-Bt) \qquad (3)$$

where "Q" is the amount of contrast agent that has yet to be reperfused, and again "A" and "B" are constants derived from curve-fitting the data. Other models of perfusion, and other methods of comparison to estimate the amount of contrast agent in a region, can also be used.

A sixth aspect of this invention relates to combining destruction pulses with subharmonic imaging. Subharmonic imaging may provide unique abilities to distinguish between contrast agents and surrounding tissue, because while contrast agents may generate subharmonics at conventional diagnostic ultrasound power levels, tissue will not. Imaging using subharmonics is described in a co-pending U.S. patent application Ser. No. 09/282,603, entitled "Medical Diagnostic Ultrasound Imaging System and Method with Fractional Harmonic Seed Signal," filed on Mar. 31, 1999, which is assigned to the assignee of the present invention and hereby incorporated by reference.

Although subharmonic imaging is frequently performed with a seed signal, it can be performed with or without a seed signal. Since subharmonic signals are typically not generated by tissue, it may be advantageous to combine subharmonic signals with fundamental signals to provide a background image, as described in a co-pending U.S. patent application Ser. No. 08/838,920, entitled "Ultrasound Imaging Enhancement Methods and Systems," filed on Apr. 11, 1997, which is assigned to the assignee of the present invention and hereby incorporated by reference. It may also be advantageous to combine subharmonic signals with harmonic signals to provide a background image, as described in a co-pending U.S. patent application, entitled "Contrast Agent Imaging with Subharmonic and Harmonic Signals in Diagnostic Medical Ultrasound," filed on the same day as this patent application, which is assigned to the assignee of the present invention and hereby incorporated by reference.

For example, referring to FIG. 5, if ultrasonic transducer 506 has an overall bandwidth from 1.5 to 4 megahertz (MHz), and the contrast agent has a resonance frequency of about 2 MHz, then beamform controller 502 sets up ultrasound system 500 for imaging with subharmonics using the following parameters. In this case, ultrasound system 500 can transmit an ultrasound pulse centered at 4 MHz, a pulse length with a Gaussian shaped envelope which has a 6 dB fractional bandwidth of 10%, and a transmit power corresponding to a mechanical index (MI) of 1.0. In this case, the transmit frequency is set to about twice the resonance frequency, because that is where the threshold for subharmonic generation is lowest. Programmable receive beamformer 505 is set up to receive signals at the first subharmonic frequency, 2 MHz, and filter signals at the fundamental frequency, 4 MHz. This can be done by demodulating the received signal by 2 MHz, so that the subharmonic frequency resides at baseband, and applying a filter with a 6 dB bandwidth of about 500 kilohertz and about 50 dB of rejection at the fundamental frequency, so that the fundamental signal is effectively removed. The exact demodulation frequency must be modified to account for frequency downshift due to tissue attenuation. For example, in this case, an initial demodulation frequency of 2 MHz could be set, and the demodulation frequency could be decreased by 100 Hz for every 1 mm of depth. Of course, these parameters should be optimized properly for subharmonic imaging. Finally, the gain must be set high enough in programmable receive beamformer 505 to display the subharmonic signal.

Because subharmonic signals are not generated by tissue, they could potentially provide excellent contrast between contrast agent and tissue. This is very useful in detecting and quantifying the presence of contrast agent. By combining subharmonics with destruction pulses, physiological functions, such as perfusion, can be measured.

For example, the firing of destruction pulses can be triggered off an ECG signal or timer, and subharmonics could be substantially continuously imaged to measure the reflow of contrast agent into a region of interest. Alternatively, both the destruction pulses and imaging pulses can be triggered. All of the methods previously described for using destruction and imaging pulses to assess physiological function using contrast agents can be applied to subharmonics. For example, by measuring the amount of contrast agent using subharmonics after destruction, perfusion parameters can be estimated by modeling perfusion with an exponential function, as described earlier.

Various or all aspects of the preferred embodiments described above can be combined for improved contrast agent imaging. In a particularly preferred embodiment, the system images at a low power, either in continuous or triggered mode, so that contrast agent is not substantially destroyed (i.e., at least about 70% and preferably at least 90% of the contrast agent is not destroyed). At some time, one or more HPRF destruction frames are fired. This destruction frame firing is triggered from a timer or a physiological signal, such as an ECG signal or a respiratory signal. These HPRF destruction frames consist of high power, HPRF pulses designed to destroy contrast agent. The HPRF destruction pulses are swept across the imaged tissue, transmitted across several lines and with several transmit foci on each line. Additionally in a preferred embodiment, multi-beam capability exists to transmit pulses in different directions or multiple pulses in the same direction. After the HPRF destruction frames are transmitted, the system returns to imaging at low power. Images are acquired in a specific sequence and then compared to assess perfusion. Several specific imaging sequences which allow such comparisons are described below.

In a first sequence, an imaging frame is acquired, followed by an HPRF destruction frame. Then, a series of imaging frames is acquired afterwards. In the expression below, "I" stands for an imaging frame, and "D" stands for an HPRF destruction frame. An example is given below:

$$I_0 \, D \, I_1, I_2, I_3, \ldots I_n \quad (4)$$

Then each of the imaging frames $I_1, I_2, I_3, \ldots I_n$ is compared to the original frame, $I_0$. In this case, the reference image $I_0$ is substantially or fully perfused with contrast agent. Comparisons of the reference image with subsequent images will indicate the amount of contrast agent that is perfusing into the region after the destruction frame. In essence, a curve can be drawn at each point in the image to indicate the amount of perfusion of contrast agent. For cardiac applications, the number of frames that are used must be kept low, however, so that there is not excessive motion between these frames and the original frame, $I_0$. However, for other applications, the number of imaging frames that are compared to the original frame can be quite high, lasting a number of seconds after the destruction frame.

The second sequence is similar to the first, except the process is repeated after n number of frames. An example is given below:

$$I_0 \, D \, I_1 \, I_2 \, I_3 \ldots I_n \, D \, I_{n+1} \, I_{n+2} \, I_{n+3} \ldots \quad (5)$$

This imaging sequence will generate a series of curves as described above to indicate the amount of perfusion of contrast agent.

A third sequence combines either of the above with gating from a physiological signal, such as an ECG signal. An example is given below:

$$I_0 \, D \, I_1 I_2 I_3 \ldots I_n \, I_{n+1} \, I_{n+2} \, I_{n+3} \ldots I_p \, I_{p+1} \, I_{p+2} \, I_{p+3} \quad (6)$$

Here, $I_0$, $I_n$ and $I_p$ are all triggered at the same point on the R-wave of an ECG signal. In this case, the images $I_n$ and $I_p$ which are compared to the original image $I_0$ are acquired at the same point of the ECG signal. Images $I_0$, $I_n$ and $I_p$ are continuously acquired, but only images around the same point of the ECG signal are compared to image $I_0$. Also, only in the first set of images is a destruction frame present. Therefore, the perfusion of contrast agent is observed over a longer range of time than for methods using a destruction frame for every set of images, such as for every cardiac cycle. This process is repeated after some set number of heart beats. This sequence can also involve triggering from a timer rather than a physiological signal so that, for example, images are acquired every second and compared to the original frame.

Yet another sequence involves triggering both the imaging frames and destruction frames from an ECG signal, where the two triggers are based on a different integer number of heartbeats. For example, imaging frames are triggered and acquired once every heartbeat, while destruction frames are fired every 5 heartbeats. An example is given below:

$$I_0\ D\ I_1\ I_2 I_3\ I_4\ I_5\ D \qquad (7)$$

Here, each imaging frame is triggered from the same point of the R-wave.

Another set of sequences is similar to those discussed above, but instead of comparing a frame with the frame immediately preceding the destruction frame, a frame is compared to the frame immediately following the destruction frame. For example, analogous to the first sequence described, frames $I_2, I_3, I_4, I_5$ are compared to $I_1$ instead of $I_0$. In this case, the reference frame is a frame devoid or substantially devoid of contrast agent rather than a frame fully or substantially perfused with contrast agent. Again, the re-flow of contrast agent over time is observed. This same approach for comparing the first image following the destruction frame to other images can be applied to the other imaging sequences as well.

An alternative sequence involves imaging at high power immediately before and after HPRF destruction frames. In this case, the system images continuously at a low power so that contrast agent is not substantially destroyed. At some time triggered by a time trigger or some physiological signal, such as an ECG signal or a respiratory signal, a high power imaging frame is transmitted. Then, one or more HPRF destruction frames are fired, followed by one or more high power imaging frames. The system then returns to low power imaging until the next trigger. The advantage of this over the first sequence is that the higher the transmit power of the imaging pulses used to obtain an imaging frame, the more clearly the contrast agent is seen, for some contrast agents.

Another embodiment of the invention involves the use of destruction pulses on individual ultrasound lines instead of destruction frames. In this approach, an imaging pulse is fired along an ultrasound image line. Then a series of HPRF destruction pulses are sent along the same line. As discussed above, these destruction pulses are sent very rapidly, since the system does not have to wait for them to return and be processed. These HPRF destruction pulses are fired for a variety of different focal depths to ensure contrast agent destruction along the whole line. Then a second imaging pulse is sent along the same line, and the received signal is compared to the received signal from the first pulse.

Another embodiment involves the use of destruction blocks. A block is a set of lines. A destruction block is a set of destruction pulses fired into a block. For example, a set of imaging pulses, a set of HPRF destruction pulses and a second set of imaging pulses are fired into the block for comparing the signals received from the imaging pulses before and after the destruction of the contrast agent in the block.

Whether destruction pulses, blocks, or frames are used, there must be a pause between the HPRF destruction pulses and the imaging pulses to remove artifacts from the destruction pulses. The artifacts from the destruction pulses are either caused by reverberations or by not waiting for the pulses to die down. Furthermore, if Doppler processing is used, pulses must be fired in order to set the reverberation environment correctly. For destruction frames, such pauses and imaging pulse firings cause a negligible reduction of the system frame rate, while for destruction blocks, they cause a larger reduction in the system frame rate. However, these pauses and imaging pulse firings cause a greatly reduced system frame rate when destruction pulses are fired only along one line at a time.

An alternative embodiment of the invention provides a user-interface, preferably a graphical user interface (GUI), where a doctor or sonographer presses a button on a screen or keyboard, clicks on a mouse, trackball or touchpad, or otherwise selects an option on the user-interface, which will instruct the ultrasound system to generate and transmit HPRF destruction pulses. There may be occasions when a doctor wants to override a programmed sequence of ultrasound pulse firings and individually control the firing of destruction pulses. That is, rather than using a programmed sequence of HPRF destruction pulses, the doctor independently activates the firing of HPRF destruction pulses from the GUI.

Many of the embodiments of the invention described herein do not require HPRF destruction pulses. In an alternative embodiment, the system images continuously without substantially destroying contrast agent, and at a time triggered by a physiological signal (e.g., an ECG signal or a respiratory signal) or a timer, a series of destruction pulses is fired to substantially destroy contrast agent. The system then returns to normal imaging. This is the approach described in FIG. 8, but without HPRF destruction pulses. Similarly, as shown in FIG. 9, a system can both image and transmit destruction pulses in triggered mode, where the two triggers are invoked at different times, keyed to fixed points of a physiological signal or a timer signal, without using HPRF destruction pulses.

Another embodiment not requiring HPRF pulses involves firing a sequence of imaging and destruction pulses such that a first image is acquired, a destruction frame is fired, and a second image is acquired for comparison to the first image, wherein the entire sequence is triggered from a source, such as an ECG signal. In this case, image brightness is used to gauge the amount of contrast agent that has perfused over that trigger interval. Such comparisons can be made using any of the imaging and comparison approaches described earlier.

Of course, all of these approaches are improved by using HPRF signals. Another approach to improve destruction of contrast agent involves using chirp signals, which can increase the time duration of a pulse without reducing the bandwidth of the pulse. Using HPRF chirp signals may further enhance destruction of contrast agent. In particular, this invention can be combined with the use of chirp signals or coded excitation as described in co-pending U.S. patent application Ser. No. 09/282,510, entitled "Medical Ultrasound Diagnostic Imaging Method and System with Non-linear Phase Modulation Pulse Compression," filed Mar. 31, 1999, and/or co-pending U.S. patent application Ser. No. 09/283,346, entitled "Medical Ultrasound Diagnostic Imaging System Using Coded Transmission Pulses", filed Mar. 31, 1999. Both patent applications are assigned to the assignee of the present invention and are incorporated by reference.

The exemplary embodiments described herein are for purposes of illustration and are not intended to be limiting. For example, while an ECG signal is the most frequently discussed physiologic signal source for triggering destruction or imaging pulses, other cardiac signals or respiratory signals can also be used for triggering destruction or imaging pulses. Moreover, the sequence of steps for firing imaging pulses and destruction pulses could be altered from what is disclosed and still achieve the intended benefits of the invention. Still further, one of skill in the art will appreciate that the system block of FIG. 5 and the flowcharts of FIGS. 8 and 9 are intended to illustrative and not limiting. Specific details of implementation may be varied without departing from the scope of the invention. For example, the system, beamformer and display controller can be optionally integrated into a single controller, or, in appropriate alternative architectures, dispensed with entirely. Likewise, transmit and receive beamformers can be optionally integrated; and while it is preferred that they be programmable, this is not necessary in order to carry out the invention. Likewise, the memory and comparator are optional in some embodiments of the invention. Finally, while destruction pulses are defined herein as not being used for imaging or display, it will be apparent to one of ordinary skill in the art that displaying such pulses on an auxiliary display or even in an irrelevant manner on the imaging display itself (e.g., in the first centimeter or so of the extended field of view) will be within the scope of this invention. Therefore, those skilled in the art will recognize that other embodiments could be practiced without departing from the scope and spirit of the claims set forth below.

What is claimed is:

1. A method for destroying contrast agent in a human or animal with medical diagnostic ultrasound equipment, comprising the step of using a multi-beam beamformer to simultaneously fire a plurality of beams of destruction pulses in a region of interest of said human or animal.

2. The method of claim 1 wherein at least two beams of destruction pulses are fired at a rate faster than the rate required for ultrasound to travel to and return from the farthest boundary of the region of interest.

3. The method of claim 1 wherein at least two beams of destruction pulses are fired at different power levels.

4. The method of claim 1 wherein at least two beams of destruction pulses are fired at different focal depths.

5. The method of claim 1 wherein at least two beams of destruction pulses are fired on different lines.

6. The method of claim 1 wherein at least two beams of destruction pulses are fired at staggered times.

7. The method of claim 1 wherein at least two beams of destruction pulses are fired at staggered times on the same line.

8. An ultrasound system for destroying contrast agent in a human or animal with medical diagnostic ultrasound equipment, comprising a multi-beam beamformer operable to simultaneously fire a plurality of beams of destruction pulses in a region of interest of said human or animal, and a transducer connected to receive signals from the multi-beam beamformer.

9. The system of claim 8 wherein the multi-beam beamformer is operable to fire at least two beams of destruction pulses at a rate faster than the rate required for ultrasound to travel to and return from the farthest boundary of the region of interest.

10. The system of claim 8 wherein the multi-beam beamformer is operable to fire at least two beams of destruction pulses at different power levels.

11. The system of claim 8 wherein the multi-beam beamformer is operable to fire at east two beams of destruction pulses at different focal depths.

12. The system of claim 8 wherein the multi-beam beamformer is operable to fire at least two beams of destruction pulses on different lines.

13. The system of claim 8 wherein the multi-beam beamformer is operable to fire at least two beams of destruction pulses at staggered times.

14. The system of claim 8 wherein the multi-beam beamformer is operable at least two beams of destruction pulses at staggered times on the same line.

15. A method for using ultrasound to destroy contrast agent in a bounded region of interest in a human body, comprising the steps of:

firing a plurality of destruction pulses into the region of interest at a rate faster than the rate required for receiving reflections from the farthest boundary of the region of interest; and substantially destroying contrast agent in the region of interest using the plurality of destruction pulses.

16. The method of claim 15 wherein the step of firing the plurality of destruction pulses includes firing pulses with a mechanical index greater than 0.6.

17. The method of claim 15 wherein the step of firing the plurality of destruction pulses includes firing pulses with a mechanical index greater than 1.0.

18. The method of claim 15 wherein the step of firing the plurality of destruction pulses includes firing pulses with a mechanical index greater than 1.5.

19. The method of claim 15 wherein the step of firing the plurality of destruction pulses includes changing a transmit parameter between the firings of destruction pulses.

20. The method of claim 19 wherein the step of firing the plurality of destruction pulses includes changing at least one of the following parameters between the firings of destruction pulses: transmit focus, transmit frequency, transmit direction, transmit pulse length, and transmit power.

21. The method of claim 15 wherein the step of firing the plurality of destruction pulses includes simultaneously firing a plurality of beams of destruction pulses.

22. The method of claim 21 wherein the step of firing the plurality of beams of destruction pulses includes firing destruction pulses in different directions.

23. The method of claim 15 further comprising the step of triggering the firing of the plurality of destruction pulses from a timer or physiological signal.

24. The method of claim 15 further comprising the step of activating a destruction pulse by a user-interface option selected by an operator.

25. The method of claim 15 further comprising the steps of:

firing a plurality of imaging pulses; and receiving and processing the plurality of imaging pulses.

26. The method of claim 25 further comprising the step of calculating perfusion parameters from a plurality of imaging pulses.

27. The method of claim 25 further comprising the step of triggering at least one imaging pulse.

28. The method of claim 27 further comprising the steps of transmitting a first set of one or more imaging pulses before transmitting the plurality of destruction pulses, and transmitting a second set of imaging pulses after transmitting the plurality of destruction pulses.

29. The method of claim 28 wherein the first set of imaging pulses and the plurality of destruction pulses are transmitted along a line.

30. The method of claim 28 wherein the first set of imaging pulses and the plurality of destruction pulses are transmitted throughout a block.

31. The method of claim 28 wherein the first set of imaging pulses and the plurality of destruction pulses are transmitted throughout a frame.

32. The method of claim 25 wherein an image is displayed based on received reflected energy at a harmonic or a subharmonic of the transmit frequency band.

33. The method of claim 25 further comprising the step of estimating parameters related to perfusion as a function of the reflected energy from at least two of the transmitted imaging pulses.

34. The method of claim 25 wherein the imaging pulse is transmitted at a sufficiently low power level to avoid destroying a substantial fraction of contrast agent bubbles.

35. The method of claim 25 wherein a plurality of imaging pulses are transmitted in succession.

36. The method of claim 25 further comprising the step of generating a plurality of images and comparing at least two images from the plurality of images.

37. The method of claim 25 further comprising the steps of generating a plurality of images and spatially or temporally filtering at least one of the plurality of images.

38. The method of claim 25 further comprising the steps of acquiring a first image before the destruction frame is fired and acquiring a second image after the destruction frame is fired.

39. The method of claim 38 further comprising the step of comparing the first image with the second image.

40. The method of claim 39 further comprising the step of displaying an output based on the comparison.

41. The method of claim 39 further comprising the step of deriving a perfusion parameter from the comparison of the plurality of images.

42. The method of claim 39 wherein the comparison is performed and displayed in a graphical form.

43. The method of claim 25 further comprising the steps of substantially continuous non-destructive imaging, alternating with destroying contrast agent with destruction pulses triggered from a timer or a physiological signal.

44. The method of claim 43 further comprising the step of comparing two images from the substantially continuous non-destructive imaging step.

45. The method of claim 43 wherein destruction pulses are triggered repeatedly at a cycle equal to a selected number of beats from an ECG signal.

46. The method of claim 43 wherein destruction pulses are triggered from a selected number of cycles of a physiological signal.

47. The method of claim 25 further comprising the steps of:
triggering imaging pulses from a first trigger; and
triggering destruction pulses from a second trigger.

48. The method of claim 47 wherein the first trigger is generated every first integer number of heartbeats from a cardiac signal and the second trigger is generated every second integer number of heartbeats from a cardiac signal, wherein the first and second integers can be the same or different, provided that the first and second triggers are not generated simultaneously.

49. The method of claim 25 further comprising the steps of:
triggering imaging pulses from an ECG or timer signal; and
triggering destruction pulses from an ECG or timer signal.

50. The method of claim 28, further comprising the step of comparing a received signal from the first set of imaging pulses to a received signal from the second set of imaging pulses.

51. The method of claim 15 wherein the step of firing the plurality of destruction pulses includes firing at a plurality of different focal depths on a line to achieve substantial destruction of the ultrasound contrast agent along the line.

52. An ultrasound system for generating images from within a body, the system comprising:
a transmit beamformer for transmitting HPRF destruction pulses and transmitting imaging pulses; and
a receive beamformer for receiving reflected energy responsive to the transmitted imaging pulses.

53. The system of claim 52 further comprising an image processor for generating an image responsive to the reflected energy.

54. The system of claim 52 further comprising means for estimating perfusion parameters from the reflected energy.

55. The system of claim 52 wherein the transmit beam former is a multi-beam transmit beamformer.

56. The system of claim 52 wherein the transmit beamformer alternately transmits a series of imaging pulses and a series of destruction pulses, either or both series of pulses triggered from a timer or a physiological signal.

57. The system of claim 52 wherein the series of destruction pulses is triggered repeatedly at a cycle equal to a selected number of beats from a cardiac signal.

58. The system of claim 52 wherein the receive beamformer receives reflected energy at a harmonic or subharmonic frequency band of the transmitted imaging pulses.

59. The system of claim 56 wherein a first trigger is generated every first integer number of heartbeats from a cardiac signal and a second trigger is generated every second integer number of heartbeats from a cardiac signal, wherein the first and second integer numbers can be the same or different, provided that the first and second triggers are generated at different times.

60. The system of claim 52 further comprising:
means for triggering imaging pulses from an ECG or timer signal; and
means for triggering destruction pulses from an ECG or timer signal.

61. The system of claim 52 further comprising means for activating a destruction pulse by a user-interface option selected by an operator.

62. The system of claim 53 wherein the image processor comprises a Doppler processor or a B-mode processor.

63. The system of claim 52 further comprising means for:
firing a first imaging pulse, firing at least one HPRF destruction pulse and then firing a second imaging pulse, then comparing a first received signal from the first imaging pulse to a second received signal from the second imaging pulse.

64. The system of claim 52 further comprising means for:
firing at least one destruction pulse, then firing a plurality of imaging pulses, then comparing a first received signal from a first imaging pulse to a second received signal from a second imaging pulse.

65. The system of claim 63 or 64 further comprising a display for displaying the comparison of the first and second received signals.

66. The system of claim 52 wherein the transmit beamformer can change transmit parameters between the firings of destruction pulses.

67. A method for generating ultrasound images from within a body, comprising the steps of:
(a) repeatedly transmitting a plurality of destruction pulses triggered at a fixed point of a physiological signal to destroy contrast agent;
(b) transmitting and receiving a plurality of imaging pulses between sets of destruction pulses; and
(c) displaying the received signals from the imaging pulses.

68. The method of claim 67 wherein at least two destruction pulses are transmitted at a rate faster than the rate required for ultrasound to travel to and return from the farthest boundary of the region of interest.

69. The method of claim 67 wherein the step of firing the plurality of destruction pulses includes changing at least one of the following parameters between the firings of destruction pulses: transmit focus, transmit frequency, transmit direction, transmit pulse length, and transmit power.

70. The method of claim 67 further comprising the step of generating a plurality of images and comparing at least two images from the plurality of images.

71. The method of claim 70 further comprising the step of deriving a perfusion parameter from the comparison of images.

72. The method of claim 67 wherein the step of firing the plurality of destruction pulses includes simultaneously firing a plurality of beams of destruction pulses.

73. The method of claim 67 wherein step (b) comprises imaging substantially continously without substantially destroying contrast agent.

74. The method of claim 67 wherein step (b) comprises transmitting and receiving a plurality of triggered imaging pulses between sets of destruction pulses, wherein the plurality of imaging pulses are triggered at a different time from the plurality of destruction pulses.

75. The method of claim 74 wherein step (b) further comprises transmitting and receiving a plurality of imaging pulses repeatedly triggered every m beats at a first fixed point of a cardiac signal and step (a) further comprises transmitting a plurality of destruction pulses repeatedly triggered every n beats at a second fixed point of a cardiac signal, wherein m and n are integers that can be equal or different and the two fixed points can be at the same or different parts of the cardiac cycle.

76. An ultrasound system for generating ultrasound images from within a body, comprising:
a beamformer for repeatedly generating a plurality of destruction pulses triggered at a fixed point of a physiological signal to destroy contrast agent;
a transducer for transmitting the plurality of destruction pulses and transmitting and receiving a plurality of imaging pulses between sets of destruction pulses; and
a display for displaying the received signals from the imaging pulses.

77. The ultrasound system of claim 76 wherein the beamformer generates at least two destruction pulses at a rate faster than the rate required for ultrasound to travel to and return from the farthest boundary of the region of interest.

78. The ultrasound system of claim 76 wherein the beamformer can change at least one of the following parameters between the firings of destruction pulses: transmit focus, transmit frequency, transmit direction, transmit pulse length, and transmit power.

79. The ultrasound system of claim 76 further comprising means for generating a plurality of images and means for comparing at least two images from the plurality of images.

80. The ultrasound system of claim 76 further comprising means for deriving a perfusion parameter from the comparison of images.

81. The ultrasound system of claim 76 wherein the beamformer is a multi-beam beamformer that can simultaneously fire a plurality of beams of destruction pulses.

82. The ultrasound system of claim 76 wherein the transducer can transmit imaging pulses substantially continously without substantially destroying contrast agent.

83. The ultrasound system of claim 76 further comprising a transducer to transmit and receive a plurality of triggered imaging pulses between sets of destruction pulses, wherein the plurality of imaging pulses are triggered at a different time from the plurality of destruction pulses.

84. The ultrasound system of claim 76 further comprising a transducer to transmit and receive a plurality of imaging pulses repeatedly triggered every m beats at a first fixed point of a cardiac signal and a beamformer to generate a plurality of destruction pulses repeatedly triggered every n beats at a second fixed point of a cardiac signal, wherein m and n are integers that can be equal or different and the two fixed points can be at the same or different parts of the cardiac cycle.

85. An ultrasound system for imaging with ultrasound contrast agent, comprising:
means for imaging continously without substantially destroying contrast agent;
means for triggering, from a time trigger or some physiological signal, firing of one or more destruction frames with a plurality of destruction pulses; and
means for returning to imaging continuously until the next trigger.

86. A method for imaging with ultrasound contrast agent, comprising the steps of:
(a) transmitting a first plurality of imaging pulses into a body in the presence of contrast agent;
(b) collecting a first frame of imaging data;
(c) transmitting a plurality of destruction pulses into the body to destroy contrast agent;
(d) transmitting a second plurality of imaging pulses into a body;
(e) collecting a second frame of imaging data; and
(f) displaying the second frame of imaging data with the first frame of imaging data to enable an operator to compare the first and second frames, wherein steps (a), (c) and
(d) are triggered from a physiological signal or timer.

87. The method of claim 86 wherein a first imaging frame is collected, a plurality of destruction pulses is transmitted, a second imaging frame is collected, and the first and second imaging frames are displayed.

88. The method of claim 86 wherein a first imaging frame is collected, a plurality of destruction pulses is transmitted, a second imaging frame is collected, and data derived from the first and second imaging frames is displayed.

89. The method of claim 86 wherein a plurality of destruction pulses is transmitted, a first imaging frame is collected, a second imaging frame is collected, and the first and second imaging frames are displayed.

90. The method of claim 86 wherein a plurality of destruction pulses is transmitted, a first imaging frame is collected, a second imaging frame is collected, and data derived from the first and second imaging frames is displayed.

91. A method for imaging with ultrasound contrast agent, comprising the steps of:
(a) transmitting a first plurality of imaging pulses into a body in the presence of contrast agent;
(b) collecting a first frame of imaging data;
(c) transmitting a plurality of destruction pulses into the body to destroy contrast agent;
(d) transmitting a second plurality of imaging pulses into a body;
(e) collecting a second frame of imaging data; and
(f) comparing the second frame of imaging data to the first frame of imaging data;
wherein steps (a), (c), and (d) are triggered from a physiological signal or timer.

92. The method of claim 91 wherein a first imaging frame is collected, a plurality of destruction pulses is transmitted, a second imaging frame is collected, and the first and second imaging frames are compared.

93. The method of claim 91 wherein a first imaging frame is collected, a plurality of destruction pulses is transmitted, a second imaging frame is collected, and the first and second imaging frames are subtracted.

94. The method of claim 91 wherein a first imaging frame is collected, a plurality of destruction pulses is transmitted, a second imaging frame is collected, and the first and second imaging frames are combined.

95. The method of claim 91 wherein a plurality of destruction pulses is transmitted, a first imaging frame is collected, a second imaging frame is collected, and data derived from the first and second imaging frames is compared.

96. The method of claim 91 wherein a plurality of destruction pulses is transmitted, a first imaging frame is collected, a second imaging frame is collected, and the first and second imaging frames are subtracted.

97. The method of claim 91 wherein a plurality of destruction pulses is transmitted, a first imaging frame is collected, a second imaging frame is collected, and the first and second imaging frames are combined.

98. A system for imaging with ultrasound contrast agent, comprising means for:

(a) transmitting a first plurality of imaging pulses into a body in the presence of contrast agent;

(b) collecting a first frame of imaging data;

(c) transmitting a plurality of destruction pulses into the body to destroy contrast agent;

(d) transmitting a second plurality of imaging pulses into a body;

(e) collecting a second frame of imaging data; and (f) displaying the second frame of imaging data with the first frame of imaging data to enable an operator to compare the first and second frames, wherein steps (a), (c) and (d) are triggered from a physiological signal or timer.

99. A system for imaging with ultrasound contrast agent, comprising means for:

(a) transmitting a first plurality of imaging pulses into a body in the presence of contrast agent;

(b) collecting a first frame of imaging data;

(c) transmitting a plurality of destruction pulses into the body to destroy contrast agent;

(d) transmitting a second plurality of imaging pulses into a body;

(e) collecting a second frame of imaging data; and (f) comparing the second frame of imaging data to the first frame of imaging data, wherein steps (a), (c), and (d) are triggered from a physiological signal or timer.

100. The system of claim 99 further comprising means for displaying the first and second imaging frames or data derived from the first and second imaging frames.

101. A method for imaging with ultrasound contrast agent within a body, comprising the steps of:

(a) transmitting a plurality of destruction pulses;

(b) transmitting a plurality of imaging pulses at a transmit frequency band; and (c) displaying an image based, at least in part, on received energy at a subharmonic of the transmit frequency band.

102. The method of claim 101 wherein step (a) further comprises triggering the firing of the plurality of destruction pulses.

103. The method of claim 101 wherein step (b) further comprises triggering the firing of the plurality of imaging pulses.

104. The method of claim 101 wherein step (b) comprises imaging substantially continuously.

105. The method of claim 101 further comprising the step of deriving a perfusion parameter.

106. A method for ultrasound imaging with contrast agent, comprising the steps of:

(a) transmitting a plurality of destruction pulses;

(b) transmitting a plurality of imaging pulses at a fundamental frequency;

(c) generating a fundamental frequency intensity value;

(d) generating a subharmonic frequency intensity value; and (e) displaying display indicia as a function of both the fundamental and subharmonic intensity values.

107. An ultrasound system for generating ultrasound images from within a body, comprising:

a transducer for transmitting a plurality of destruction pulses, transmitting a plurality of imaging pulses at a transmit frequency band, and receiving energy; and a filter for passing received signals at a subharmonic of the transmit frequency band.

108. The system of claim 107 further comprising means for triggering the firing of the plurality of destruction pulses.

109. The system of claim 107 further comprising means for triggering the firing of the plurality of imaging pulses.

110. The system of claim 107 wherein the transducer transmits a plurality of imaging pulses for imaging substantially continuously.

111. The system of claim 107 further comprising a processor for deriving a perfusion parameter from a plurality of image pulses.

112. The system of claim 107 further comprising a display for displaying images.

113. An ultrasound system for generating ultrasound images from within a body, comprising:

(a) a transducer for transmitting a plurality of imaging pulses having a fundamental frequency and a plurality of destruction pulses;

(b) a processor for generating intensity values based on the fundamental frequency and a subharmonic frequency of the fundamental frequency; and (c) a display for displaying intensity values as a function of both the fundamental and subharmonic intensity values.

114. A method for ultrasound imaging with contrast agent, comprising the steps of:

(a) transmitting a plurality of destruction pulses;

(b) transmitting a plurality of imaging pulses at a harmonic frequency;

(c) generating a harmonic frequency intensity value;

(d) generating a subharmonic frequency intensity value; and (e) displaying display indicia as a function of both the harmonic and subharmonic intensity values.

115. A method for imaging contrast agent in a human or animal with medical diagnostic ultrasound equipment, the method comprising:

(a) transmitting a plurality of pulses adapted to destroy contrast agents;

(b) transmitting a plurality of pulses adapted to image contrast agents, the pulses of (b) having at least one different parameter than the pulses of (a); and (c) transmitting a plurality of pulses adapted to limit destruction of contrast agents, the pulses of (c) having at least one different parameter than the pulses of (a) and (b).

116. The method of claim 115 further comprising:

(d) triggering (a) and (b).

117. The method of claim 116 wherein (d) comprises triggering in response to a physiological signal.

118. The method of claim 116 wherein (c) comprises transmitting substantially continuously.

119. The method of claim 116 wherein (a) comprises transmitting with one of a rate faster than the rate required for ultrasound to travel to and return from the farthest boundary of the region of interest, a higher power than (b), a transmit pulse length longer than for (b), varying pulse parameters for different pulses of (a), and combinations thereof.

120. The method of claim 116 wherein (b) comprises transmitting with a higher power than (c).

121. A method for imaging contrast agent in a human or animal with medical diagnostic ultrasound equipment, the method comprising:

(a) transmitting destruction pulses;

(b) transmitting imaging pulses; and (c) transmitting non-destructive pulses less destructive of the contrast agent than the imaging pulses.

* * * * *